United States Patent [19]

Maurer et al.

[11] 4,294,679

[45] Oct. 13, 1981

[54] FLAT ELECTROCHEMICAL SENSOR, AND METHOD OF ITS MANUFACTURE

[75] Inventors: Helmut Maurer, Schwieberdingen; Klaus Müller, Tamm; Ernst Linder, Mühlacker; Franz Rieger, Aalen-Wasseralfingen; Günther Stecher, Ludwigsburg, all of Fed. Rep. of Germany

[73] Assignee: Robert Bosch GmbH, Stuttgart, Fed. Rep. of Germany

[21] Appl. No.: 145,738

[22] Filed: May 1, 1980

[30] Foreign Application Priority Data

Jul. 14, 1979 [DE] Fed. Rep. of Germany ....... 2928496

[51] Int. Cl.$^3$ ........................................... G01N 27/58
[52] U.S. Cl. ............................... 204/195 S; 29/592 R
[58] Field of Search ........................... 204/195 S, 1 S; 29/592 R

[56] References Cited

U.S. PATENT DOCUMENTS 4,126,532 11/1978 Takao et al. .................... 204/195 S
4,157,282 6/1979 Riddel ............................... 204/1 T

*Primary Examiner*—G. L. Kaplan

*Attorney, Agent, or Firm*—Frishauf, Holtz, Goodman & Woodward

[57] ABSTRACT

To apply a measured quantity of air to the electrodes applied to a plate-like solid electrolyte body, which may be a chip on a carrier or may, itself, form the carrier, grooves, flutes, ducts, or depressions are formed in the carrier and/or a cover plate, the grooves terminating at an edge portion with access to the gas to be supplied, and having a size such that their clear height is preferably in the lower micron region, and a width, preferably under 1 mm, and particularly between 0.2 and 0.4 mm. The higher limits are applicable to apply, for example, air to a reference electrode, to apply ambient oxygen thereto; the lower limits are appropriate when operating the sensor as a polarographic sensor, in which the diffusion limited current, upon application of a bias voltage, is an analog measure of the oxygen concentration in the gas, and the gas supply to the electrode must be suitably controlled to prevent saturation conditions. The grooves may be formed, for example, by sandblasting or by applying insulating material in the form of posts, ridges, and the like, on the respective element, filling the space therebetween with a filler substance which, upon subsequent sintering, escapes, thus leaving the voids forming the grooves, depressions, and the like.

34 Claims, 17 Drawing Figures

FLAT ELECTROCHEMICAL SENSOR, AND METHOD OF ITS MANUFACTURE

Cross reference to related applications, assigned to the assignee of the present application:
U.S. Ser. No. 06/121,632, filed Feb. 14, 1980, MULLER et al
U.S. Ser. No. 06/121,599, filed Feb. 14, 1980, MAURER.

The present invention relates to an electrochemical sensor, and more particularly to such a sensor suitable to determine the oxygen content of gases, especially of combustion exhaust gases, and particularly of the exhaust gases from internal combustion engines, such as automotive-type engines; and to economical and efficient methods of its manufacture.

BACKGROUND AND PRIOR ART

Various types of electrochemical sensors to determine oxygen content in gases have been proposed. In such sensors which are particularly adapted for use with internal combustion engines, a housing, preferably of metal, holds the sensor element itself in rigid and sealed position. The sensor element as such includes an oxygen ion conductive solid electrolyte, such as zirconium dioxide. In one type of construction, and this is the type to which the present invention relates, the zirconium dioxide solid electrolyte is flat, in form of a plate. It may be self-supporting or positioned on a support plate or carrier. Two spaced film-type or layer-like porous electrodes are placed on the electrolyte, spaced from each other. At least one of those electrodes is exposed to the gas to be tested.

A simple type of sensor of the general construction is described in U.S. Pat. No. 4,157,282, Riddel. Two electrodes are applied to a plate-like solid electrolyte, both electrodes being exposed to the gas to be measured. The sensor operates in accordance with a potentiometric principle, that is, upon exposure of one electrode to the test gas and another electrode to a reference gas, a voltage will appear across the electrodes which is, respectively, indicative of presence or absence of oxygen in the gas to be tested. It has also been proposed to construct an oxygen sensor which has a carrier on which a layer-like solid electrolyte body is applied to which, in turn, an electrode is applied exposed to the exhaust gas and a second electrode to a material having a predetermined oxygen partial pressure. A layer-like heating element is also provided in German Patent Disclosure Document DE-OS No. 27 42 278, corresponding to U.S. Pat. No. 4,126,532, TAKAO et al.

Other types of sensors are polarographic sensors described, for example, in U.S. application Ser. No. 6,093 of Jan. 24, 1979, Dietz, assigned to the assignee of the present application, and now abandoned. This sensor has a reference electrode which is exposed to a reference gas—typically ambient air or, rather, the oxygen in ambient air; the measuring or sensing electrode is covered with a material forming a diffusion barrier to oxygen molecules derived from the gas to be tested. In a polarographic sensor, the output signal will be representative of the content of oxygen in the test gas if a voltage is applied across the electrodes. Another type of polarographic sensor, in which both electrodes are exposed to the measuring gas, and which includes a heating element as described in U.S. Pat. No. 3,691,023, Ruka et al.

THE INVENTION

It is an object to improve the structure of the sensor element so it can be made industrially simply and inexpensively, has low heat capacity and thus rapid response and availability for use after down-time.

Briefly, a plate-like carrier is provided which is so arranged that, to supply gas to at least one of the two electrodes, channels are formed. The channels may be arranged on various structural elements, for example on the solid ion conductive body and/or its carrier, on a cover plate, and the like. Additional support posts or points—all of very small dimension, of course, or support ridges can be formed. The free height of the channels is within a lower micrometer range; the width of the channels is preferably below 1 mm, for example between 200 and 400 micrometers.

The channels can be formed either in the respective elements after the elements have been prepared with a smooth surface, or the channels can be formed by building up ridges, bumps or projections on the respective element.

The channels can be coated at their bottom or side walls, for example, with a material which catalyzes the gas equilibrium, for example a platinum metal, gold, silver, nickel, or the like.

The construction lends itself readily for combination with flat, film or layer-like heating elements which can be constructed in such a manner that they form a part of the catalytically active channels or grooves.

In accordance with a feature of the invention, the electrodes are applied to a carrier which, at least in part, includes oxygen ion conductive material, such as zirconium dioxide; in a subsequent step, ridges or support posts of material which is gas-impervious and capable of being sintered is applied on the electrodes; such material is, for example, a ceramic such as aluminum oxide, glass or ceramic glass, applied in accordance with a desired pattern not only on the electrodes but, preferably, also on conductive connecting tracks and on the remaining portions of the carrier or substrate. To prevent collapse of the free space, a filler material which, upon sintering, will be removed or chemically dissolved, such as carbon black with alcoholic additives, is then applied, and over the assembly there is placed a cover of a material which is gas-impervious and capable of being sintered, for example a glass-ceramic. The entire assembly is then sintered, which frees the ducts from the filler and exposes the electrodes to the space between the ducts which are now free.

In accordance with another feature of the invention, the electrodes are preformed to have thickened or ridged portions in those regions where the ducts are to be placed; upon application of a cover plate over the electrodes, and sintering the entire assembly, the thickened portions of the electrodes will melt into the porous support carrier, leaving the free spaces in those regions where the thickened portions had been, thus forming the ducts or channels.

The sensor in accordance with the invention has the advantage over other sensors and sensors known in the prior art that it can be made easily by inexpensive, readily controlled industrial processes; due to its low heat capacity, it has rapid start-up time. The spaces into which gas can penetrate are small, so that the sensor is sensitive to even small variations in oxygen concentration of the gas to be measured. The sensor construction is useful both for polarographic as well as for potentiometric sensors; when used with a reference gas, the ducts can supply the reference gas to one of the electrodes; it is also possible to so construct the ducts or grooves that they will have a predetermined molecular diffusion resistance for oxygen molecules. The small space in which the test gas and/or the measuring gas is supplied also effectively decouples the sensor with respect to temperature changes of the electrodes exposed to the measuring gas.

Coating the inside of the ducts or grooves with catalytically active material has the additional advantage that the sensor is especially sensitive and intensively catalytically active in precisely that region where measuring is taking place, so that the gas equilibrium can be effectively determined.

Drawings, illustrating preferred examples to an enlarged scale.

Figure 1:
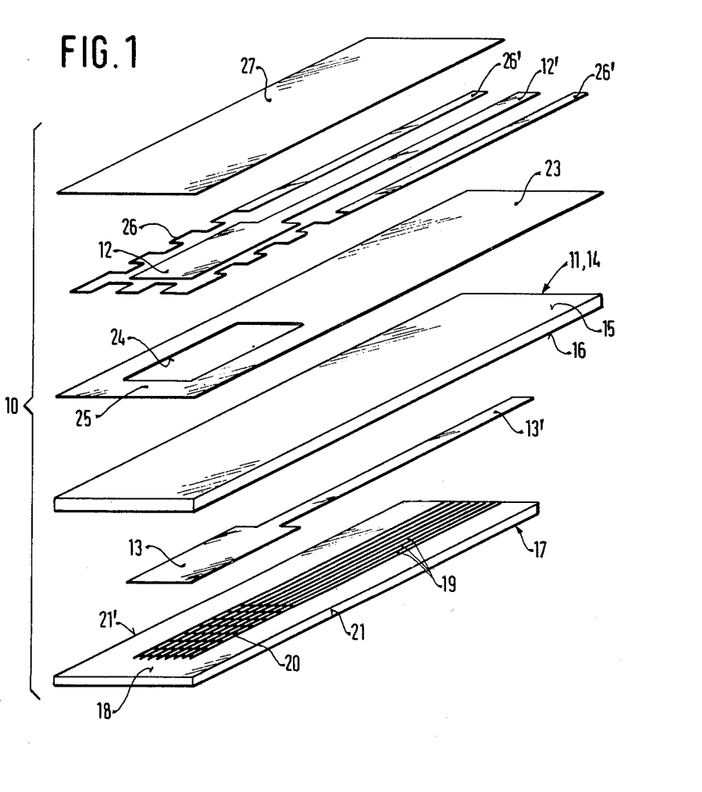
FIG. 1 is an exploded view of the sensor element of a potentiometric sensor in which electrodes are located on both sides of a carrier element, a layer-like heating element is provided, and pressed-in flat channels are provided for supply of oxygen from the air to the reference electrode.
Figure 1A:
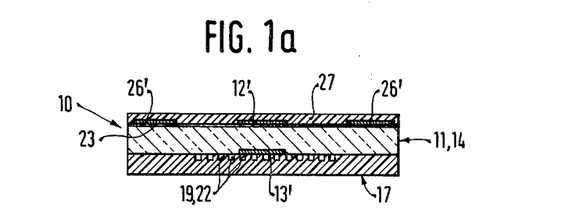
FIG. 1a is a cross section through the sensor of FIG. 1 in the region of the conductive tracks, to a still greater enlarged scale.

The sensor 10 of FIGS. 1 and 1a is used to determine oxygen partial pressure in gases, particularly in gases resulting from a combustion process and especially in the exhaust gases of internal combustion engines. It is adapted to be mounted in the longitudinal opening or bore of a housing (not shown), preferably made of metal, and which, for example, in principle can be constructed as shown in U.S. Pat. No. 4,157,282, Riddel, the disclosure of which is therefore incorporated herein by reference or, for example, as shown in copending application assigned to the assignee of the present invention, U.S. Ser. No. 121,598, filed Feb. 14, 1980, MULLER et al.

The sensor element 10 is so secured in the housing that it extends in part into a duct or conduit through which the gas, the oxygen content of which is to be determined, will flow. The sensor thus with one end, hereinafter the "sensing end portion", extends directly into the interior of the gas line. Depending on the application, however, the sensor can also be placed in a branch from the main exhaust gas line of an engine, or another combustion process. The sensor 10 operates in well known manner as an electrochemical potentiometric cell. It has a solid electrolyte body 11 made of oxygen ion conductive material, for example zirconium dioxide, and two electrodes 12, 13 applied thereto, preferably in form of layers. Electrode 12 is the measuring electrode, and electrode 13 is a reference electrode. The solid electrolyte body 11, in the example made of stabilized zirconium dioxide, has the form of a flat plate and simultaneously forms the carrier 14 for the sensor 10. Its dimensions, in an example suitable for use to determine the oxygen content in the exhaust gases of internal combustion engines of the automotive type is, for example, about 5 cm long, about 6 mm wide, and about 0.8 mm thick. These dimensions, of course, are not critical and can be matched to specific applications.

The measuring electrode 12, which is located as a layer on the measuring end portion of one flat side 15 of the carrier 14, is made of a porous metal which catalyzes the gas equilibrium of the gas reaching the same; platinum, or a platinum-type metal is suitable, and a thickness of about 10 $\mu$m is appropriate. The reference electrode 13 which likewise is a layer of about 10 $\mu$m thickness is applied at the measuring gas portion to the second flat side 16 of the carrier 14. Preferably, it is made of a material which has less catalyzing effect with respect to the gas equilibrium, for example is made of gold. The two electrodes 12, 13 are applied to the carrier 14 so that they are in vertical alignment, that is, are covering each other. They may be applied by any well known method, such as by printing, vapor deposition, or some other suitable manner. The measuring electrode 13 can be electrically connected by a conductive track 13' which extends to the portion of the carrier 14 remote from the measuring end portion, hereinafter the "holding portion" of the sensor - since it is that part which is usually retained within the housing in which the sensor element is positioned. The conductive track 13' may be integral with the electrode 13 and consist of the same material and of the same thickness, but it need not. An electrically insulating cover plate 17 of approximately 0.6 mm thickness is located over the reference electrode 13 and the conductive track 13'. Cover plate 17 is wider than the reference electrode 13 and leaves only a narrow end portion of the track 13' exposed to permit an electrical connection to be made thereto. The cover plate 13 is made, for example, of aluminum oxide.

In accordance with a feature of the invention, the flat side 18 of cover plate 17 facing the reference electrode 13 is formed with a plurality of longitudinally extending grooves, channels, flutes, or striae which are closed at the measuring end portion, but open at the holding end portion, and which extend over the area which is covered by the reference electrode 13. In the region of the reference electrode 13, the portions of the longitudinal grooves 19 are crossed by cross grooves 20, terminating in advance of the lateral edges 21, 21' of the cover plate 17. The longitudinal grooves 19 and the cross grooves 20 have a depth of about 30 μm, a width of about 0.3 mm, and can be made by any well known process such as by pressing them in while the cover plate 17 is still deformable, by grinding, sand-blasting, laser burn-out, or other processes. Upon manufacture of the sensor 10, all elements are sintered together and the grooves 19, 20 in the cover plate 17 form a system of covered ducts 22 (see FIG. 1a) together with the carrier 14 and the reference electrode 13 and its conductive track 13'. This duct or groove system 22 permits access of oxygen in ambient air to the reference electrode 13.

Grooves similar to grooves 19, 20 also could be, selectively, formed in the carrier 14, and, if desired and depending on the particular application, grooves can be formed in the carrier 14 as well as in the cover plate 17. The cross-sectional profile of the grooves 19, 20 can be rectangular—as in the example illustrated—but it need not be; it can be trapeze-shaped or half-round, for example. The arrangement of the longitudinal grooves 19, or the cross grooves 20 parallel to the longitudinal edges of the carrier 14, likewise is not critical; the grooves can be arranged in an undulating, zig-zag pattern, or as otherwise desired. The duct 22, particularly when used to supply reference air, may have larger dimensions than those given above; both the width as well as the depth can be increased within the limits of structural strength of the materials involved.

The upper (FIG. 1) flat side 15 of the solid electrolyte body 11 has an electrically insulating layer 23 applied thereto, by any suitable and well known method, for example printing, vapor deposition, or the like. A suitable material is aluminum oxide of about 20 μm thickness, formed with a window-like opening 24. The layer-like measuring electrode 12 is located in that window opening. The layer-like electrode 12 is connected to a conductive track 12' and is positioned on the insulating layer 23 and thus, even if the solid electrolyte body is heated and becomes somewhat electrically conductive, the track 12' is insulated with respect to the track 13' of electrode 13. Erroneous measurement results in the region of the sensor which is not part of the sensing electrodes thus are prevented.

A heating element 26 is applied to the frame portion 25 of the insulating plate 23 to surround the measuring electrode 12 with some distance. Typically, the heating element 26 is a meander-like or zig-zag like extending track of platinum of about 10 μm, connected by conductive tracks 26' with the holding end portion of the sensor 10 for subsequent connection to an electrical heating supply circuit (not shown). A porous, electrically insulating layer 27 is applied over the measuring electrode 12 and the heating element 26, in accordance with any well known method, for example by printing, vapor deposition, or the like. The porous cover plate 27 covers the electrode 12 and the tracks 12', 26', with the exception of a narrow end portion permitting electrical connection to the tracks. Cover layer 27, for example, is made of aluminum oxide or magnesium spinel, about 15 μm thick, and prevents corrosion by hot gases of the measuring electrode and of the heating element 26, and the associated conductive tracks 12', 26'.

The aforedescribed elements are securely connected together by sintering and then form the sensor 10 which operates, as well known, as an oxygen ion concentration cell in accordance with potentiometric principle, with respect to oxygen of known partial pressure, derived, easiest and most typically, from the oxygen in ambient air.

The heating element 26 is not required for every sensor 10. In some cases it may be desirable, however, to use two heating elements. If this is desired, a second heating element is positioned between the cover plate 17 and the solid electrolyte 11. Of course, an insulating layer must be applied between the solid electrolyte 11 and the heating element, for example similar to the insulator 23, to prevent electrical short circuits. Such a second heating element is suitable if the position of installation of the sensor is such that the gases to which the sensor is exposed are no longer sufficiently warm to heat the sensor to its normal operating temperature of above about 400° C., or if response of the sensor immediately when it is first exposed to exhaust gases is required, that is, before the sensor could be heated by sufficiently hot exhaust gases.

The mode of operation of the sensor—as a potentiometric cell, or as a diffusion limited current polarographic sensor, in which an external bias voltage is applied, depends on the characteristics and the nature of the layer 27. If, instead of using a porous insulating cover 27, the layer 27 at least in the region congruent with the electrode 12 is made such that the passage or flow resistance of oxygen molecules therethrough is so high that the diffusion limited current principle of current flow is applicable, then the sensor can be operated in accordance with the polarographic principle. In other words, the flow resistance, or resistance to diffusion of oxygen molecules through the plate 27 where the oxygen molecules will come in contact with the electrode 12 can be arranged to permit use of the sensor to operate in the polarographic mode. The basic structural relationship of the elements can remain the same; the characteristics of plate 27, however, must change. A material suitable for plate 27 is aluminum oxide or magnesium spinel, suitably treated, however, not to have the wide pores which permit unrestricted access of gas to the electrode 12—and acting only as a protective layer—but rather presenting substantial resistance to flow passage therethrough, by migration of oxygen molecules which will eventually reach the measuring electrode 12.

Figure 2:
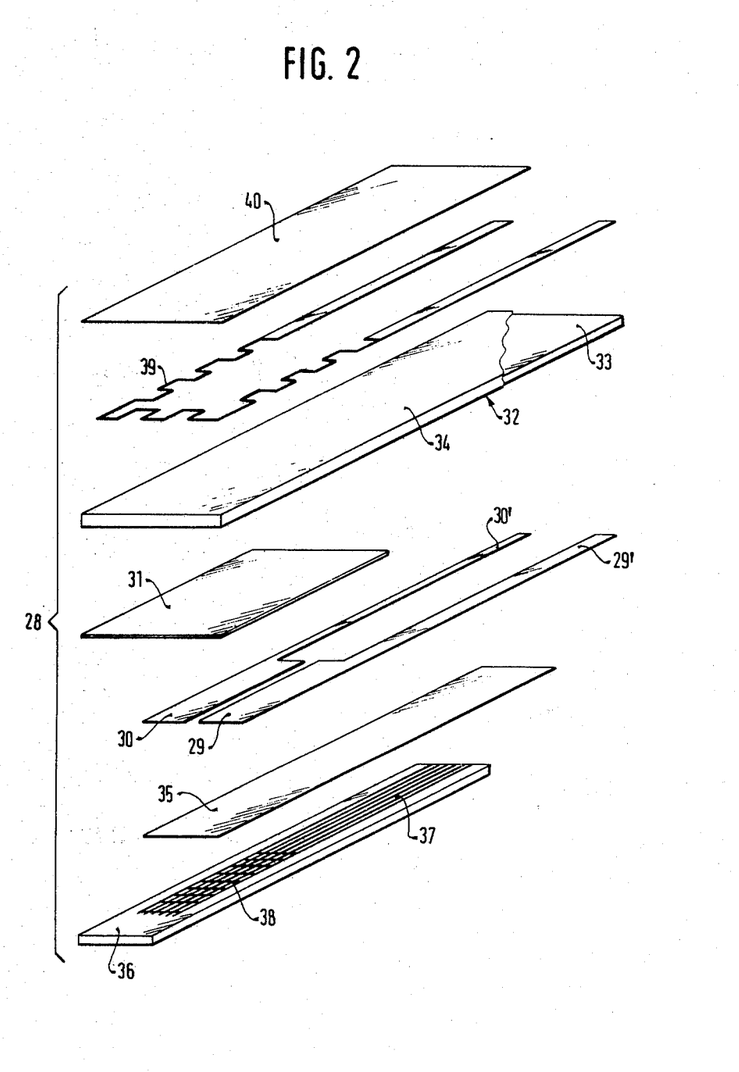
FIG. 2 is an exploded view of a sensor in which the electrodes are applied to one side of the carrier only.

Embodiment of FIG. 2: The difference between the sensor 28 (FIG. 2) and sensor 10 (FIGS. 1, 1a) essentially is this: Both the measuring electrode 29 as well as the reference electrode 30 are located on the same side—and spaced from each other—of a layer-like solid electrolyte 31 which is attached to an electrically insulating carrier 32 in accordance with any well known method—for example by printing thereon. The layer-like solid electrolyte 31 is about 0.1 mm thick and covers only a portion of the entire extent of the carrier 32, for example principally the measuring end portion thereof. Carrier 32 may be made of metal, for example a nickel alloy such as "Inconel", of about 0.3 mm thickness, coated with an insulator 34, for example aluminum oxide of 30 μm thickness. The electrically insulating layer 34 can be applied to the metallic carrier 33 which, preferably, is of sheet metal, in accordance with any well known and suitable process. The solid electrolyte material, for example stabilized zirconium dioxide, is comparatively expensive; the carrier 32 thus supports only a small quantity of the expensive solid electrolyte material. A compact carrier can also be used made, for example, of aluminum oxide or some other suitable electrically insulating material. The measuring electrode 29 with its conductive track 29' is covered with a porous, electrically insulating cover 35, which leaves only a small portion at the holding end portion of the track 29' uncovered to permit an electrical connection to be made thereto (see the examples of FIGS. 1, 1a). The reference electrode 30, as in the examples of FIGS. 1, 1a, is covered with a cover plate 36 which has longitudinal grooves, flutes or the like 37, and cross grooves 38. The cover plate 36 covers the reference electrode 30 and track 30', except for the final end portion. When sintered together, the cover plate 36, reference electrode 30, solid electrolyte 31, and carrier 32 will, together, define ducts to supply air to form a reference oxygen level opposite the reference electrode 30.

The other flat side of the carrier 32 has a layer-like heating element 39 applied thereto, covered by a porous, electrically insulating protective layer 40 to protect the heating element 39 against corrosion, as explained in connection with FIGS. 1 and 1a. In the space between the heating element 39, a further measuring or sensing element can be positioned, for example a temperature sensor, such as a thermocouple, if desired.

The other features of sensor 28 correspond to those of sensor 10 (FIGS. 1, 1a). This sensor, likewise, can be constructed to operate either as a potentiometric ion conductive cell or as a polarographic sensor operating on the diffusion limited current principle. If the sensor is to operate as a polarographic sensor, the layer 35 on the sensing electrode then must have a flow or passage resistance to oxygen molecules of such magnitude that diffusion of oxygen molecules will permit operation of the electrode in accordance with the diffusion limited current mode at the electrode.

Figure 3:
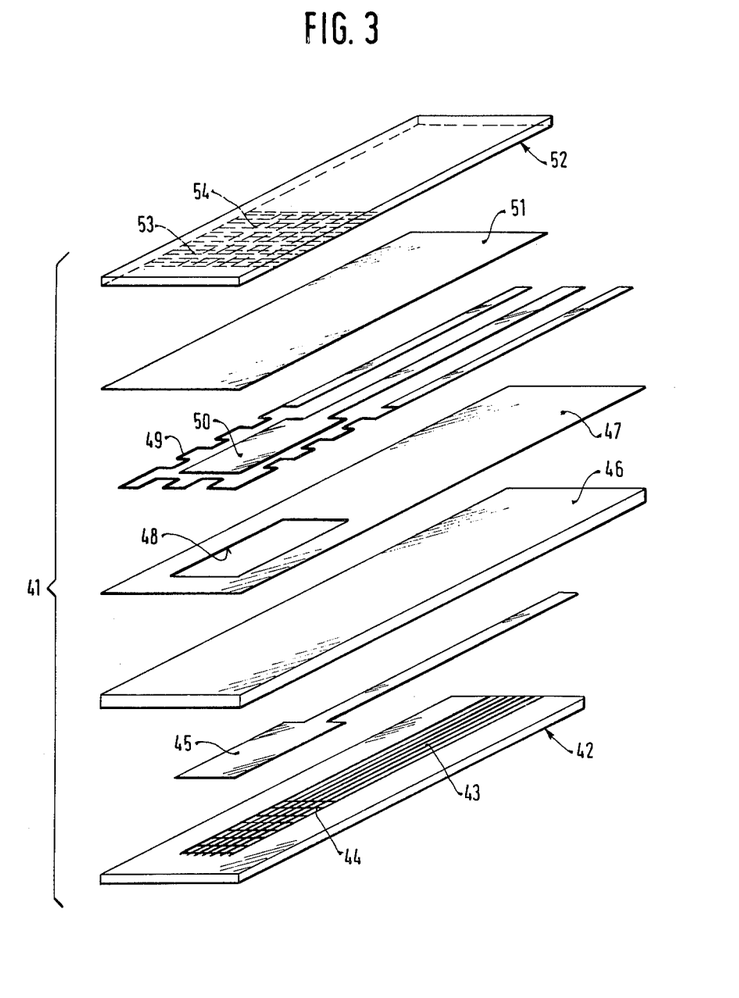
FIG. 3 is an exploded view of a sensor element for a polarographic-type sensor in which the electrodes are located on both sides of the carrier, further including a flat, layer-like heating element, with flat ducts of predetermined diffusion or flow resistance for oxygen molecules in advance of the sensing electrode, and flat ducts to supply oxygen from the air to the reference electrode.

Embodiment of FIG. 3: Sensor 41, as shown, operates in accordance with the polarographic principle; its construction is quite similar to that of the sensor 10 of FIGS. 1, 1a. Considering the sensor, with the various elements thereof from the bottom up, a cover plate 42 is formed with longitudinal grooves 43 and cross grooves 44, a reference electrode 45 is provided and applied on a plate-like solid electrolyte body 46 which, likewise, forms the main support carrier for the electrodes. Next, an electrically insulating layer 47 is applied, having a window 48, in which a sensing electrode 50 is positioned, surrounded by a heating element 49. A porous, electrically insulating cover layer 51 is applied thereover. In addition, a second cover plate 52 is located over the electrically insulating layer 51, that is, over the measuring electrode 50 and the heater element 49. Cover plate 52 corresponds essentially to cover plate 42, both with respect to shape as well as material, and is formed with a plurality of cross grooves 53 which are open to the longitudinal ends of the cover plate 52, and internally connected by a plurality of short longitudinal grooves 54, terminating short of the holding end portion of the plate 52, preferably only covering about the extent of the electrode 50. Grooves 53, 54 have a depth of about 20 μm, and a width of about 0.2 mm. They provide a predetermined passage, or migration or flow resistance for oxygen molecules in the measuring gas, which will be practically independent of gas pressure; thus, oxygen molecules can flow or migrate to the measuring electrode 50. Depending on the nature of the application, the area covered by the grooves 53, 54 can be coated with a material which catalyzes the gas balance. Such a coating (not shown) may be a platinum metal, or the like. The various elements are applied against each other, and sintered together.

The cover plate 42 on the reference electrode 45 could be replaced by a corrosion-protective layer if oxygen reference, for example derived from ambient air, is not needed. Cover plate 42, then, would only act as a corrosion-protective layer.

The sensor structure of FIG. 3 can be utilized also to construct a sensor operating on the potentiometric principle—in which case the grooves which permit passage of measuring gas to the electrode 50 through the porous cover plate 51 will be made somewhat larger so that gas flow is essentially unrestricted, without impairing the protective functions thereof. Aluminum oxide, magnesium spinel, or the like, are suitable for plate 52, as well as for plate 51 when constructed to be suitably porous, respectively.

Figure 4:
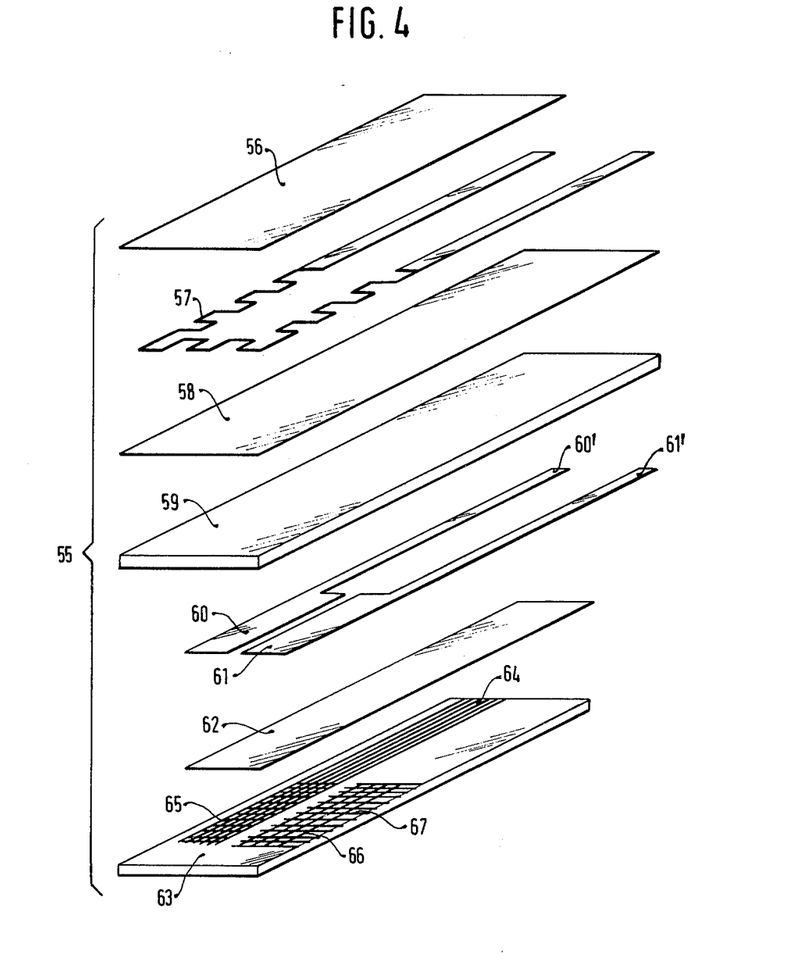
FIG. 4 is an exploded view of a sensor similar to that of FIG. 3 in which, however, the electrodes are applied to one side of the carrier only.

Embodiment of FIG. 4: A sensor 55 which, as desired, and as specifically constructed, can operate either in accordance with the polographic or potentiometric principle, is quite similar to the sensor 28 (FIG. 2). Considering FIG. 4, from the top down, the sensor has a cover plate or layer 56, a heater element 57, an electrically insulating layer 58, a carrier 59 which, in the example, simultaneously is the solid electrolyte body, a reference electrode 60 with a reference conductive track 60', a measuring electrode 61, adjacent thereto and having a conductive track 61', and a cover layer 62 which protects the measuring electrode 61 and the conductive track 61' against corrosion, and a cover plate 63. Cover plate 63 is as wide as the carrier 59. In accordance with a feature of the invention, and similar to the cover plate 42 of FIG. 3, the cover plate 63 is formed with longitudinal grooves 64 and cross grooves 65 over the reference electrode 60. In addition, the cover plate 63 is formed with longitudinal partial grooves 67 and cross grooves 66. The second system of grooves 66/67 provides a predetermined diffusion passage or diffusion flow resistance for oxygen molecules of the sensing gas and, if desired, can be coated with a material catalyzing the gas equilibrium. Such coating is not shown, and may, for example, consist of platinum metal. The cross grooves 67 extend to the lateral sides of the carrier 63. The partial longitudinal grooves only form connecting ducts between the cross grooves 67. The grooves 66, 67 are about 20 μm and 0.2 mm wide; the grooves 64, 65 over the reference electrode 60 may be deeper and wider, for example 0.1 mm deep, and 1 mm wide.

If it is not desired to apply oxygen from ambient air as a reference gas, then cover plate 63 can have a groove system similar to the grooves 66/67 formed therein opposite the reference electrode 60, in which the cross grooves extend to the end of the cover plate 63. Alternatively, that portion of the cover plate 63 which carries the grooves 64/65 can be omitted and the entire region replaced by a porous cover layer protecting the electrode against corrosion.

Figure 5:
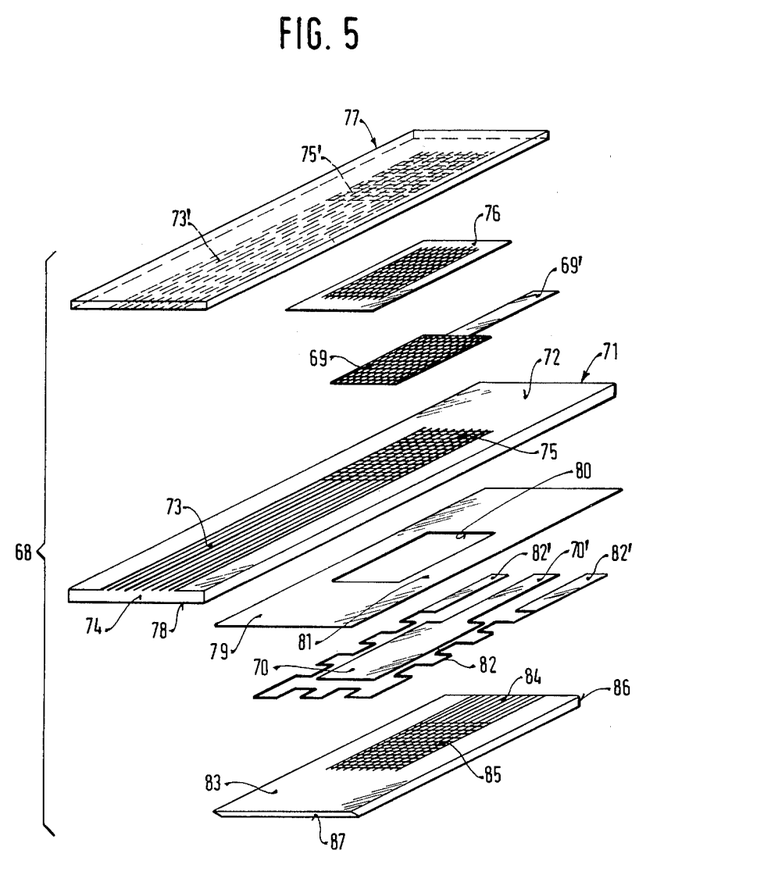
FIG. 5 is an exploded view of a sensor element for a polarographic sensor in which electrodes are located on both sides of the carrier at the portion of the carrier remove from the measuring end, with a layer-like heater element, with narrow ducts with predetermined flow or passages resistance for oxygen molecules for the measuring electrode, and ducts to supply oxygen from the air for the reference electrode.

Embodiment of FIG. 5: Sensor 68 is preferred for a sensor operating in the polarographic mode, although the structure can be modified or adapted to permit the sensor to operate in the potentiometric mode. The advantage of sensor 68 is the placement of the sensing electrode 69 and of the reference electrode 70, and removal of the electrodes from direct position within the stream of the measuring gases. The recess of the electrodes 69, 70 results in decrease of the influence of the measuring gas temperatures and, consequently, decrease of changes in such temperatures, and consequently less stress on the sensing electrode 69, the reference electrode 70 and the attached conductive tracks 69', 70'. In sensor 68, the plate-like solid electrolyte 71 simultaneously forms a carrier, on the upper flat side 72 of which (FIG. 5) a plurality of longitudinal grooves 73 are formed. These grooves are about 10 μm deep, 0.2 mm wide, and extend from the end edge 74 at the measuring end portion up to the central portion of the solid electrolyte body 71 and, possibly, within the region of the holding end portion. A plurality of cross grooves 75 interconnect the longitudinal grooves 73 in a region congruent with that of the measuring electrode 69. Measuring electrode 69, with its conductive track 69', additionally has a porous cover applied thereover, for example of magnesium spinel, to protect the electrode 69 against corrosion. A cover plate 77 which covers the grooves 73, 75 is applied over electrode 69, cover 76 and the carrier 71. The side of cover plate 77 which faces the grooves 73, 75 likewise can be formed with grooves 73', 75' which, preferably, match the position or location of the grooves in the carrier plate 71 and have about the same depth and width. For additional catalyzation of the gas balance, the region covered by the grooves 73', 75', and possibly even the region of the groove 73, which is opposite the measuring electrode 69, can have a layer of a platinum metal (not shown, since so thin) applied thereto.

The lower flat side 78 of the solid electrolyte plate 71 is covered with an electrically insulating layer 79, formed with a window 80 positioned opposite the measuring electrode 69. The reference electrode 70 is located within the window 80, applied in accordance with any well known and suitable process, preferably by printing. A conductive track 70' extends over the insulating plate 79. If desired, and depending on the application, sensor 68 can have a heater 82, in layer form, applied on the frame 81 surrounding the window 80 of the plate 79. Heater connecting tracks 82' extend from the heater 82. The assembly is closed off by a cover plate 83. At the side facing the reference electrode 70, longitudinal grooves 84 and cross grooves 85 are formed therein, covering the region of reference electrode 70, and having a depth of about, for example 30 μm, and a width of about 0.3 mm. The longitudinal grooves 84 extend out of cover plate 83 at the holding end portion and, together with the cross grooves 85, permit application of oxygen from ambient air to the reference electrode 70.

The plates are assembled facing each other and sintered together.

The electrodes 69, 70 can be located so far inward on the carrier 71 that they extend even within the housing (not shown) of the sensor; in such a construction, the lower cover plate 83 could be omitted and, instead thereof, a corrosion protective layer can be applied over reference electrode 70 with the conductive track 71 and over the heater element 82 with the conductive tracks 82'. The cover plate 83 and the corrosion protective layer, of course, terminate just short of the end portions of the respective conductive tracks to permit an electrical connection to be made thereto.

The sensor can operate either with ambient air as a reference oxygen level or without ambient air. If no ambient air reference is needed, the longitudinal grooves are not extended to the edge 86 of the holding end portions but, rather, the plate 83 would be reversed over its plane by 180° for example, so that the grooves 84 extend to the edge 87 at the measuring end portion.

Various changes and modifications may be made; for example, electrodes 69, 70, rather than being located at both sides of the carrier plate 71, can be located adjacent each other within a central region thereof, for example similar to the arrangement shown in FIG. 2 or FIG. 4. The cover plate thereover then must be formed with separate groove systems for the measuring electrode and the reference electrode; a heating element, which may be required, can then be applied on the support plate in corrosion-protected arrangement. The cover plate covering the two electrodes may be similar to plate 63, FIG. 4, except that the position of the crossed groove systems would be located more centrally on the plate, and the longitudinal grooves 67 may extend to the edge of the measuring end portion of the sensor. Locating both electrodes at a single side of the carrier to which a solid electrolyte layer has been applied has the advantage that a smaller quantity of the relatively expensive solid electrolyte material suffices, and the second flat side of the carrier provides space not only for the heating element but also for an additional sensor, such as a temperature sensing element.

Methods of manufacture, with reference to FIGS. 6-10: The method will be explained in connection with a sensor 88 (FIG. 6) operating on the polarographic principle, but is equally suitable for a potentiometric sensor which has a plate-like oxygen ion conductive solid electrolyte 89, each of the lateral sides 90, 91 of which has an electrode 92, 93 applied thereto. Ducts 94, 94' are additively applied. The first flat side 90 of carrier 89 (FIG. 6) has a measuring electrode 92 of platinum applied thereto by printing. Conductive track 95, likewise applied by printing, extends to the holding end portion from measuring electrode to a terminal region formed as a terminal tab 96. A meander-like heating element 97 is applied around the measuring electrode 92, connected with a pair of conductive tracks 97' extending to the holding end portion of the carrier 89. An electrically insulating layer 98, for example aluminum oxide, electrically insulates the heating element 97 and the associated pair of conductive tracks 97' with respect to the oxygen ion conductive solid electrolyte, for example made of stabilized zirconium dioxide, which becomes gradually electrically conductive as it is being heated. The materials used and the respective dimensions correspond to those described in connection with the sensors 10, 28, 41, 55, 68. The arrangement, preferably, had been presintered.

Figure 6:
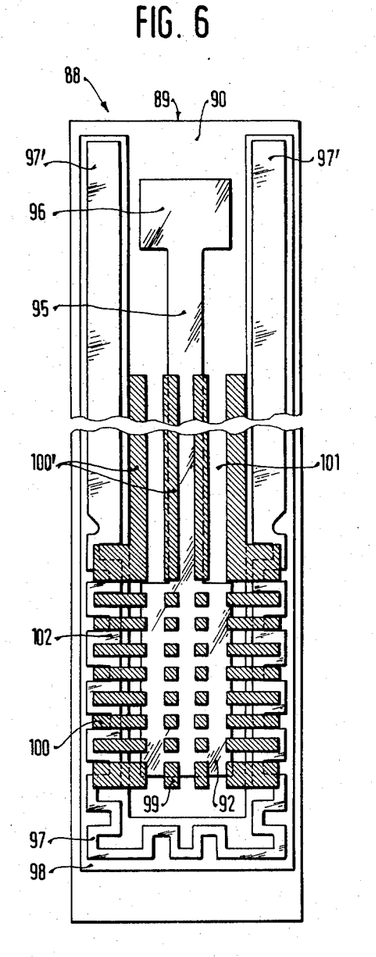
FIGS. 6, 7 and 8 are top views of the flat side of a platelike carrier of a sensor element for a potentiometric sensor with a measuring electrode, ducts leading thereto and having catalytically active portions, and a layer-like heating element and illustrating, sequentially, steps in the manufacture of the element.
Figure 7:
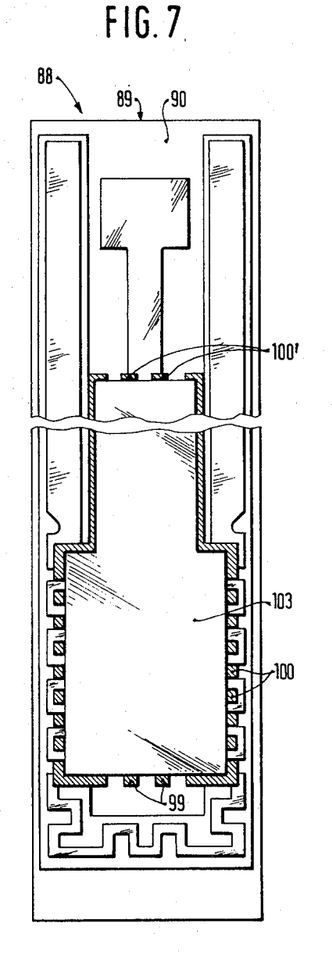

In the region of the carrier 89 taken up by the electrode 92, and surrounding this region, a plurality of supports 99 and cross ridges 100 and longitudinal ridges 100' are applied made of a gas-impervious material such as ceramic, glass, or ceramic glass. These support posts 99 and ridges 100, 100' are preferably applied by printing, in such a manner that therebetween longitudinal grooves 101 and cross grooves 102 will be defined. The grooves, flutes, striae, or depressions 101, 102 between the respective posts and ridges are so placed that, upon a subsequent sintering process, they will have a depth of about 20 μm and a width of about 0.2 mm. The cross ridges 100, preferably, are so positioned that between adjacent cross ridges 100, a portion of the heater element 97 will be arranged, which is uncovered. When the sensor 88 is finished, the heater element 97, which is made of platinum, simultaneously provides the catalytic material to catalyze the gas balance. The heater element may, however, also consist of another suitable metal than platinum, for example a platinum metal, or a suitable alloy.

The posts 99 and/or the ridges 100, 100' of glass or ceramic glass additionally can have additives applied thereto or consist entirely of such materials which have a suitable catalytic effect. Depending on the use to which the sensor is to be put, platinum metals, gold, silver and nickel are suitable. Since the catalytically active ridges 100, 100' may be conductive, they then must be insulated from the meander-like heating element 97 by an electrically insulating layer (not shown), for example aluminum oxide, which need be located only in the region of the heater and which covers the ridges 100, 100'. If no heater element 97 is needed, the respective posts 99 and/or ridges 100, 100' can be directly applied on the carrier 89.

The subassembly so obtained is sintered at a temperature of preferably about in the order 1400° C. which, however, is not critical and may be varied readily ±250° C. The next step and the process is filling the spaces between the posts and ridges, that is, filling the grooves 101, 102 with a filler (not shown). A suitable filler, for example, is carbon black or soot, with an alcoholic additive which, upon subsequent sintering or firing, can escape. To ensure escape of the filler, and to prevent any damage to the sensor 88 upon subsequent sintering, the cross grooves 102 are important. Posts 99, ridges 100, 100', and grooves 101, 102 filled by filler (not shown) are then covered in the next step (FIG. 7) by a cover plate 103, for example by applying plate 103 by printing. Plate 103 consists of a gas-impervious material capable of being sintered, for example ceramic glass. Catalytically active alloys may be contained therein, for example as in the ridges 100, 100', and in the posts 99; or the plate 103 may carry a suitable coating. Plate 103 is, for example, of 0.4 mm thickness. Its overall size, preferably, is so limited that it does not entirely cover the outer edge portions of the sensor 88, carrying the posts 99 and the ridges 100, 100'; the end portions of the ridges and posts are not entirely covered but, rather, an end region of about 0.3 mm is left uncovered.

The subassembly is then sintered, depending on the material of the cover layer 103 at a temperature of between 800° to 1350° C. The filler material—not shown—will now escape, and thus the cross grooves 94 (FIG. 8) and the longitudinal grooves 94' (FIG. 10) will result. The grooves or ducts 94, 94' in the polarographic sensor 88 are brought to the proper size such that the flow or diffusion resistance for oxygen molecules is appropriate, for example by application of a second cover 105 thereover (FIG. 8) which more or less covers the end portions of the grooves adjacent the remaining posts 99 and ridges 100, 100', to more or less close off the respective grooves. The second cover 105, made of gas-impervious ceramic, ceramic glass or glass, can have a thickness of 0.3 mm and only leaves open the ducts 94 extending to the longitudinal side of the sensor 88 to permit controlled ingress of measuring gas.

The sensor can also be made in another manner: On the sintered posts 99 and ridges 100, 100' (FIG. 6), a plate of about 0.2 mm thickness of ceramic, glass or metal is soldered. The materials facing each other, that is, the materials of the posts 99 and ridges 100, 100', must be compatible to accept the solder, and it is necessary to coat the respective elements with glass or metal, respectively, to permit soldering or fusion together. The use of filler and sintering of the first cover plate 103 can thus be omitted. The remaining steps of the process are the same, and the cover plate, itself, will have such a configuration that the openings through which the measuring gas can pass or diffuse are of appropriate size.

Figures 8, 9:
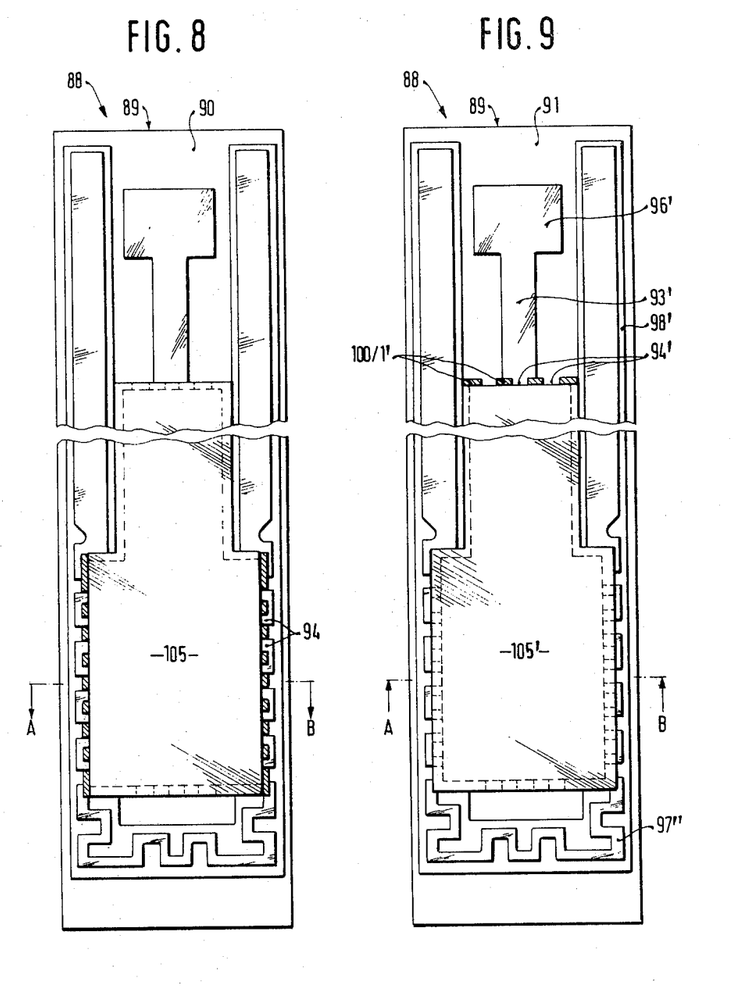
FIG. 9 is a bottom view of the carrier of the sensor of FIGS. 6-8, i.e. the side 180° removed with respect to the side of FIGS. 6-8, with the reference electrode, ducts to supply oxygen from the air thereto, and a layer-like heating element.
Figure 10:
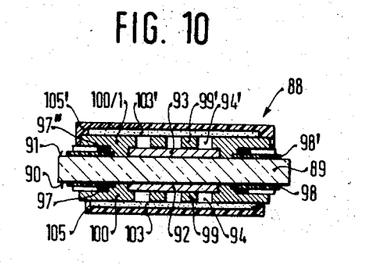
FIG. 10 is a cross section through the sensor according to lines A-B of FIG. 8, and line A'/B' of FIG. 9.

FIG. 9 shows the obverse side—with respect to FIG. 8—of the sensor 88. The second flat side 91 of the sensor 88 (see also FIG. 10) carries the reference electrode 93 with conductive tracks 93' and the connecting region or tab 96'. The second side 91 likewise carries a heater element 97" located on an electrically insulating layer 98', support posts 99', ridges 100/1, 100/1', a cover 103', and a second cover 105'. The second cover 105' leaves only those longitudinal ducts 94' open which extend to the holding end portion of the carrier 89, and closes off all the other ducts 94'. Ducts 94', in the polarographic sensor 88, are used to supply oxygen from ambient to the reference electrode 93. Posts 99' and the ridges 100/1 and 100/1' may be made of ceramic, for example aluminum oxide, glass, or similar materials. The cross section of the air supply ducts 94' can be larger than the ducts 94 for the measuring electrode 92, for example they may have a width of between 0.3 to 1 mm, and a height which may go to the order of about 0.04 mm.

The method of manufacture of flat ducts over the electrodes can be used for any type of sensor previously described, and specifically for sensors in which the electrodes are not located at the measuring end portion, but rather further towards the central portion thereof (see FIG. 5), or even shifted towards the holding end portion. Likewise, the ducts and channels can be made in this manner on sensors on which the electrodes are located on only one flat side of the carrier (FIGS. 2, 4).

Figure 11:
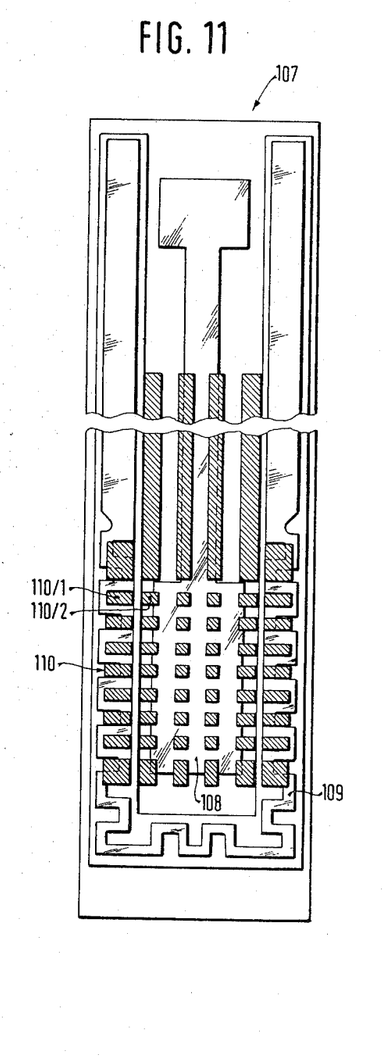
FIG. 11 is a top view of the flat side of a plate-like carrier of the sensor element for a polarographic sensor with the measuring electrode and a flat layer-like heating element, with the cover plate removed.
Figures 12, 13:
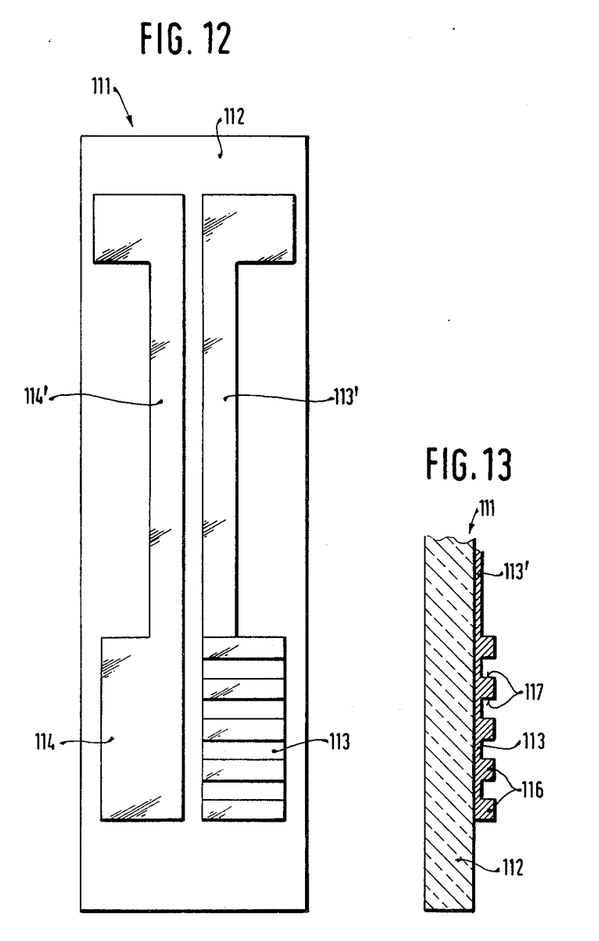
FIG. 12 is a top view of a plate-like carrier for a sensor element for a polarographic sensor with a pair of electrodes positioned on only one flat side thereof.
FIG. 13 is a cross-sectional view through the sensor of FIG. 12.
Figure 14:
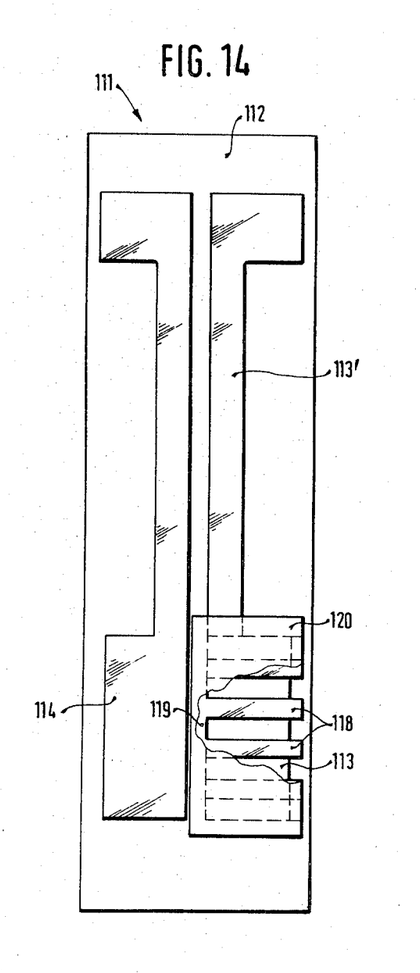
FIG. 14 is a top view of the sensor of FIG. 12 in a subsequent stage of manufacture.
Figure 15:
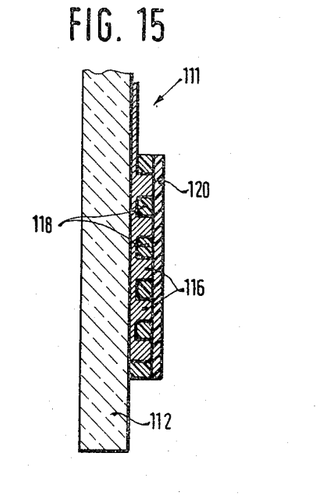
FIGS. 15 and 16 are cross sections through the sensing portion of the sensor of FIGS. 12-14, showing sequential steps in the manufacture thereof.
Figure 16:
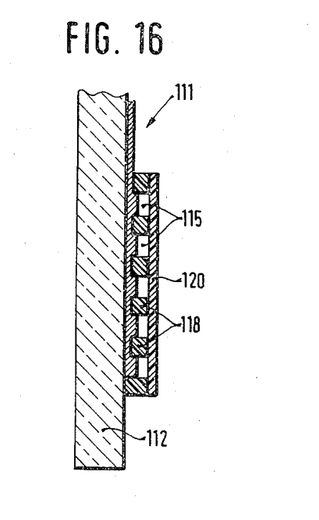

Method, with references to FIGS. 11 to 16: A flat side of a sensor 107 is shown in FIG. 11, which carries a heater element 109 and a measuring electrode 108 of a polarographic sensor. In spite of the presence of the heater element, the ridges 110, made of ceramic material or glass, should have a catalytically active alloy applied thereto. The ridges are to carry at least one cover (not shown in FIG. 11). The catalytically active alloys may, for example, be a platinum, a platinum metal, gold, silver, nickel, or the like. The heater element 109 and the sensing electrode 108 must be reliably separated electrically from each other. Thus, the ridges 110 are preferably interrupted, and especially in the sections 110/1 which are in communication with the heater element 109, and in that section 110/2 which is not in communication with the heater element 109, but rather with the measuring electrode 108. If a cover—not shown—also is to be made catalytically effective, and hence electrically conductive, the ridges 100/1 must be insulated with an electrically insulating layer with respect to the heater element 109, which is congruent at least with the ridges 110/1. The remaining construction and the method of making the sensor 107 corresponds to that previously described with respect to sensor 88. Sensor 107, of course, may be constructed also to be suitable to operate in the potentiometric mode.

A particularly suitable way to make a sensor 111 (FIG. 12) is illustrated, sequentially, in FIGS. 12–16. Sensor 111 has a plate-like carrier 112, on one major side of which the measuring electrode 113 as well as the reference electrode 114 are applied—spaced from each other. At least in region of the electrodes 113, 114, the carrier 112 is made of oxygen ion conductive electrolyte material, for example stabilized zirconium dioxide. Conductive tracks 113', 114' extend from the electrodes 113, 114. The reference electrode 114, together with the adjacent portion of conductive track 114' of the sensor 111, which operates, for example, in the polarographic mode, is exposed to the measuring gas through a porous, protective layer (not shown) which is applied in accordance with any well known process, such as by spraying, printing, or the like. The measuring electrode 113 is exposed to the gas through gas ducts 115 (see FIG. 16) which present a predetermined flow resistance for oxygen molecules, that is, which controls the passage or flow, for example by diffusion, of oxygen molecules to the electrode. The measuring electrode 113, which is made of platinum or a platinum-type metal, for example together with its conductive track 113', is applied by printing on the carrier 112 which had been presintered. The requisite thickness of the electrode in those regions where the gas supply ducts 115 should extend when the sensor 111 is finished, is obtained by sequential printing steps, for example three to four printing steps, applying platinum or a platinum metal in those regions of the measuring electrode 113.

The result will be a group of ridges or thickened areas, of about 0.25 mm width and about 0.04 mm thickness. These ridges 116 (FIG. 13) are separated by grooves flutes or the like 117. The grooves 117 are filled with a ceramic mass or with a material containing ceramic, which may contain catalytically active materials such as platinum metal, gold or silver, and which, after a subsequent sintering step, will become gas-impervious to form walls 118 within the ducts 115—see FIGS. 14 and 15. Additional limit walls 119 can be applied besides the intermediate walls 118 on the measuring electrode 113 and/or other regions of the carrier 112 and/or the conductive track 113. Such a wall 119, as seen in FIG. 4, provides for shielding of the sensing electrode 113 with respect to the reference electrode 114.

In a subsequent step, a cover 120 is printed over the ridges 116, the intermediate walls 118, and the end or limit walls 119. Cover 120 may be a ceramic, e.g. aluminum oxide, of about 0.4 mm thickness. Upon a subsequent sintering step, at about 1300° C., the sensor 111 is sintered together. The thickened portions 116 of the measuring electrode 113 will melt down during the sintering process by a distance of about 20 μm, and diffuse or melt into the porous carrier 112, to then result in the ducts 115—compare position of free ducts 115 with ridges 116 in FIGS. 16 and 15.

This method may also be used to form ducts for supply of oxygen from ambient air for the reference electrode, particularly if the sensor is used as a potentiometric sensor, or also when used as a polarographic sensor. Of course, suitable heating elements may be sintered together with the sensor to supply outside heat thereto.

Various changes and modifications may be made, and features described in connection with any one of the embodiments may be used with any one of the others, within the scope of the inventive concept.

We claim:

1. Electrochemical sensor unit for determination of oxygen content in gases, particularly exhaust gases from a combustion process, especially exhaust gases from an internal combustion engine, adapted for support by and in a metallic housing, said sensor unit being of essentially elongated plate-like form having a sensing end portion adapated for exposure to the gases and a holding end portion adapted for attachment into the housing, and an intermediate portion intermediate said end portions, said sensor units having a plate carrier element (11, 14; 31, 32; 46; 59; 71; 89; 108; 112);

a plate-like solid electrolyte body (11; 31; 46; 59; 71; 89; 108; 112) forming at least in part said carrier element;

a measuring electrode and a reference electrode forming an electrode pair (12, 13; 29, 30; 45, 50; 60, 61; 69, 70; 92, 93; 108; 113, 114), said electrodes being porous metallic layers located on said electrolyte body, spaced from each other, at least the measuring electrode being adapted to be exposed to the gases to be tested; wherein, in accordance with the invention, at least one of the electrodes is covered with a cover plate (17; 36; 63, 77; 83; 103; 103', 120), and to conduct a gas to at least one of the electrodes, depressions, grooves, ducts or flutes (22; 94, 94'; 115) are formed between the respective electrode and at least one of said cover plates said depressions, grooves, ducts or flutes being open to the gas to be admitted and dimensioned to control the quantity of gas being admitted to the respective electrode.

2. Sensor unit according to claim 1, wherein the width of the depressions, grooves, ducts or flutes is below about 1 mm.

3. Sensor unit according to claim 1, wherein the width of said depressions, grooves, ducts or flutes is in the order of between about 0.2 and 0.4 mm.

4. Sensor unit according to claim 1, 2 or 3, wherein the height of the depressions, grooves, ducts or flutes is in a lower 10-order μm range.

5. Sensor unit according to claim 4, wherein said range is in the order of between about 10 μm to 30 μm; and said depressions, grooves, ducts or flutes are exposed to the exhaust gases.

6. Sensor unit according to claim 1, wherein the width of the depressions, grooves, ducts or flutes is in the order of about 1 mm, and the depth is in the order of about 100 μm;

and said depressions, grooves, ducts or flutes are exposed to ambient air to admit oxygen to the respective electrode to permit operation of the sensor with application of reference oxygen to the respective electrode.

7. Sensor unit according to claim 1, further including ridges, posts or projections formed on the respective element, the depressions, grooves, ducts or flutes being defined by the spaces between said ridges, posts or projections.

8. Sensor unit according to claim 1, wherein the depressions, grooves, ducts or flutes (19, 20; 37, 38; 43, 44; 53, 54; 64, 65; 66, 67; 73, 75; 73', 75'; 84, 85) and defining gas supply ducts (22) are formed as depressions within at least one of said elements of the sensor (10; 28; 41; 55, 68).

9. Sensor unit according to claim 1, further comprising a material capable of catalyzing the gas equilibrium at the electrode included in at least one of the surfaces (99, 103; 118, 120) between which the depressions, grooves, ducts or flutes forming gas ducts (94; 115) are defined.

10. Sensor unit according to claim 9, wherein said material comprises at least one of the materials of the group consisting of platinum metals, gold, silver and nickel.

11. Sensor unit according to claim 10, wherein said material comprises platinum.

12. Sensor unit according to claim 9, further including a layer-like heating element adjacent the walls defining the depressions, grooves, ducts or flutes;

and wherein said heating element (97, 109) comprises at least a portion of the walls defining the catalytically active wall portions of the ducts (94).

13. Sensor unit according to claim 1, wherein the electrodes (12, 13; 29, 30) are located adjacent the sensing end portion of the unit (10; 28);

the measuring electrode (12; 29) comprises a material more highly active to catalyze the gas equilibrium than the material of the reference electrode (13; 30);

and wherein said depressions, grooves, ducts or flutes (22) are in communication with the reference electrode (13, 30) and extend to the holding end portion and are there open to the access of ambient air to permit application of oxygen from ambient air to the reference electrode.

14. Sensor unit according to claim 1, wherein the measuring electrode (50; 61, 69; 92, 113) is in direct communication with a group of ducts (53, 54; 66, 67; 73, 75; 73', 75'; 94; 115) open to the exhaust gas, said ducts being dimensioned to form a predetermined flow or passage resistance to oxygen molecules;

and conductive tracks (45, 50; 60', 61; 69', 70'; 92, 93; 113, 114) connected to the electrodes and extending to the holding end portion of the sensor unit, adapted for connection of the electrodes to a source of direct current to operate the sensor in a polarographic mode.

15. Sensor unit according to claim 14, wherein the electrodes (113, 114) of the sensor unit (111) are located adjacent the sensing end portion of the unit (111), and the reference electrode (114) is exposed to the exhaust gas.

16. Sensor unit according to claim 14, wherein the electrodes (45, 50; 60, 61) are located adjacent the sensing end portion of the sensor unit (41; 55; 88);

and the reference electrode (45; 60; 93) is in communication with ducts (43; 64; 94') open at the holding end portion of the sensor unit (41; 55; 88) to permit application of oxygen from ambient air to the reference electrode.

17. Sensor unit according to claim 14, wherein the electrodes (69, 70) are located at an intermediate portion of the sensor unit;

and wherein at least the sensing electrode (69) is in communication with ducts (73) open to and in gas flow or diffusion communication with the gases to be tested.

18. Sensor unit according to claim 14, wherein the electrodes (69, 70) are located on an intermediate portion of the sensor unit (68), the sensing electrode (69) is in communication with ducts (73) open to the gases, the oxygen content of which is to be tested, and the reference electrode (70) is exposed to oxygen from ambient air.

19. Sensor unit according to claim 1, wherein the sensor unit (10; 28; 41; 55; 68; 88; 107) includes at least one layer-formed heating element (26; 39; 49; 57; 82; 97, 97"; 109).

20. Sensor unit according to claim 1, wherein the plate-like solid electrolyte body forms said carrier plate.

21. Sensor unit according to claim 1, wherein (FIG. 2) said plate carrier element comprises a support plate extending from said sensing end portion to said holding end portion;

and said solid electrolyte body comprises a plate-like element substantially smaller than said support plate and dimensioned only to permit it being covered by the electrodes of said electrode pair.

22. Method to make an electrochemical sensor unit, for the determination of oxygen content in gases, particularly exhaust gases from a combustion process and especially exhaust gases from an internal combustion engine, adapted for support in a metallic housing, said sensor unit being essentially of elongated plate-like form having a sensing end portion adapted for exposure to the gases, a holding end portion adapted for attachment in the housing, and an intermediate portion intermediate said end portions, said sensor unit having a plate-like carrier element;

a plate-like solid electrolyte body forming at least in part said carrier element;

a measuring electrode and a reference electrode forming an electrode pair, said electrodes being porous metallic layers located on said electrolyte body, spaced from each other, at least the measuring electrode being adapted to be exposed to the gases to be tested;

and at least one cover plate element covering at least one of the electrodes, and wherein the sensor is characterized in that ducts or flutes are formed between a respective electrode and at least one of said elements, said ducts or flutes being open to a gas to be admitted and dimensioned to control the quantity of gas being admitted to the respective electrode to conduct the gas thereto, said method comprising the steps of (a) applying the electrodes (92,93) on the carrier (89); then (b) applying projecting elements (100, 100/1; 99, 99') of a gas-impervious material capable of being sintered on at least one of the electrodes and at least portions of the carrier (89), said projecting elements defining the grooves or flutes therebetween; then (c) applying a filler material in the grooves or flutes which, upon a sintering process, is volatile or dissolvable; then (d) applying a cover (103, 103') of a gas-impervious material capable of being sintered on the surface formed by the projecting elements and the filler material; then (e) sintering said sensor unit to unite the components thereof to sinter together the projecting elements and the cover and evaporate or dissolve and filler to leave the grooves or flutes free.

23. Method according to claim 22, wherein the electrodes comprise platinum, or a platinum metal.

24. Method according to claim 22, wherein the projecting elements comprise ridges or posts made of at least one material of the group consisting of aluminum oxide; a ceramic; glass and glass-ceramic.

25. Method according to claim 24, wherein the step (b) of applying the ridges or posts is in a predetermined pattern.

26. Method according to claim 22, wherein the step of applying a filler comprises applying a mixture of soot or carbon black and alcoholic additives in the grooves or flutes between the projecting elements.

27. Method according to claim 22, wherein the step of applying a cover comprises applying a ceramic glass over said surface.

28. Method according to claim 22, wherein the step of applying a cover over said surface comprises applying the cover over the surface while leaving the end portions of the projecting elements adjacent the edges of the carrier element free from cover material.

29. Method according to claim 22, further comprising an additional sintering step between steps (b) and (c) as defined in claim 21.

30. Method according to claim 22, wherein the step of applying a cover comprises applying said cover over the surface while leaving free the end portions of the projecting elements adjacent the edges of the carrier element;
and further comprising the additional step, after the sintering step, of applying an additional cover (105, 105') over the already applied cover (103, 103') and over the free end portions of the projecting elements (99, 99'; 100, 100/1), said additional cover comprising gas-impervious material capable of being sintered, and at least partially closing off at least some of the grooves or flutes (94, 94');
and then sintering the sensor including the additional cover (105, 105').

31. Method to make an electrochemical sensor unit, for the determination of oxygen content in gases, particularly exhaust gases from a combustion process and especially exhaust gases from an internal combustion engine, adapted for support in a metallic housing, said sensor unit being essentially of elongated plate-like form having a sensing end portion adapted for exposure to the gases, a holding end portion adapted for attachment in the housing, and an intermediate portion intermediate said end portions,
said sensor unit having a plate-like carrier element;
a plate-like solid electrolyte body forming at least in part said carrier element;
a measuring electrode and a reference electrode forming an electrode pair, said electrode being porous metallic layers located on said electrolyte body, spaced from each other, at least the measuring electrode being adapted to be exposed to the gases to be tested;
and at least one cover plate element covering at least one of the electrodes,
and wherein the sensor is characterized in that ducts or flutes are formed between a respective electrode and at least one of said elements, said ducts or flutes being open to a gas to be admitted and dimensioned to control the quantity of gas being admitted to the respective electrode to conduct the gas thereto,
said method comprising the steps of
(a) providing a carrier (112) which is porous, and at least in part oxygen ion conductive, and applying the electrodes (113) comprising a platinum metal on said carrier (112); then
(b) thickening those regions of the electrodes (113) over which the flutes or ducts (115) are to be positioned by forming thickened regions (116) thereof having a thickness which is a multiple of the thickness of the regions which are free from ducts or flutes; then
(c) applying a gas-impervious material comprising at least in a substantial part a ceramic in the depressions (117) between the thickened regions of the electrodes (113) to form separating walls (118); then
(d) applying a gas-impervious substance of a material capable of being sintered to form a cover (120) over the thickened portions (116) of the electrodes (113) and the separating walls (118); then
(e) sintering said sensor unit to unite the components thereof and melt the thickened portions (116) of the electrodes to penetrate into the porous carrier (112), thereby leaving free spaces beneath the cover (120) where the thickened regions (116) of the electrodes had melted down and penetrated the carrier.

32. Method according to claim 31, wherein the carrier (112) comprises a ceramic which had been presintered.

33. Method according to claim 31, wherein the step of applying the gas-impervious ceramic-containing material to form separating walls (118) further comprises the step of applying said material at selected regions over the carrier to form end or limit walls for the flutes or grooves to be formed in step (e) as claimed in claim 30.

34. Method according to claim 31, wherein the gas-impervious material comprises at least one of the materials of the group consisting of a ceramic and glass-ceramic.

* * * * *